(12) United States Patent
Pal et al.

(10) Patent No.: US 7,199,109 B2
(45) Date of Patent: Apr. 3, 2007

(54) POTENT INHIBITION OF INFLUENZA VIRUS BY SPECIFICALLY DESIGNED SHORT INTERFERING RNA

(75) Inventors: Bijay K. Pal, Arcadia, CA (US); Lynn M. Tran, Alhambra, CA (US)

(73) Assignee: Cal Poly Pomona Foundation, Pomona, CA (US)

( * ) Notice: Subject to any disclaimer, the term of this patent is extended or adjusted under 35 U.S.C. 154(b) by 0 days.

(21) Appl. No.: 11/445,573

(22) Filed: Jun. 2, 2006

(65) Prior Publication Data

US 2006/0275265 A1 Dec. 7, 2006

Related U.S. Application Data

(60) Provisional application No. 60/687,373, filed on Jun. 3, 2005.

(51) Int. Cl.
*A61K 48/00* (2006.01)
*C12N 15/63* (2006.01)
*C07H 21/04* (2006.01)
*C07H 21/02* (2006.01)

(52) U.S. Cl. .................... 514/44; 435/320.1; 536/23.1; 536/24.3; 536/24.5

(58) Field of Classification Search ..................... None
See application file for complete search history.

(56) References Cited

U.S. PATENT DOCUMENTS

2004/0242518 A1 12/2004 Chen et al.

Primary Examiner—James Schultz
Assistant Examiner—Amy H. Bowman

(74) *Attorney, Agent, or Firm*—Joseph E. Mueth, Esq.

(57) ABSTRACT

This patent application discloses siRNA sequences against the constant region of the influenza virus nucleoprotein gene comprising:

```
Sense strand:
5' UGAAGGAUCUUAUUUCUUCdTdT 3'      (SEQ ID NO: 1)

Anti sense strand:
3' dTdTACUUCCUAGAAUAAAGAAG 5'      (SEQ ID NO: 2)

Sense strand:
5' UGAAGGAUCUUAUUUCUUCGGdTdT 3'    (SEQ ID NO: 3)

Anti sense strand:
3' dTdTACUUCCUAGAAUAAAGAAGCC 5'    (SEQ ID NO: 4)

Sense strand:
5' GGAUCUUAUUUCUUCGGAGACdTdT 3'    (SEQ ID NO: 5)

Anti sense strand:
3' dTdTCCUAGAAUAAAGAAGCCUCUG 5'    (SEQ ID NO: 6)
``` said sequences being inhibitory against influenza virus in animals including humans. The invention further includes one or more of said siRNA sequences in the form of an aqueous suspension suitable for nasal inhalation. Still further, the invention includes one or more of said siRNA sequences in the form of a plasmid expressing intracellularly in animals including humans. In another aspect, the invention includes one or more of said siRNA sequences in the form of an AAV vector adapted to express intercellularly and establish a permanent inhibitory effect against influenza virus by integrating to the cellular chromosome of animals including humans. The invention also includes the administration to an animal including humans, in a therapeutically effective amount, at least one of said siRNA sequences.

11 Claims, 4 Drawing Sheets

POTENT INHIBITION OF INFLUENZA VIRUS BY SPECIFICALLY DESIGNED SHORT INTERFERING RNA

This patent claims the filing date of U.S. Provisional Patent Application Ser. No. 60/687,373, filed Jun. 3, 2005, the disclosures of which are incorporated herein by reference.

BACKGROUND OF THE INVENTION

Viruses are packets of infectious nucleic acid surrounded by protective coats which lack metabolic energy due to the absence of independent metabolism, and are incapable of growth by protein synthesis or reproduction apart from living cells. They have a prokaryotic genetic apparatus and usually contain either DNA or RNA, but not both and are usually covered by a protein shell or capsid which protects the nucleic acid.

The influenza or *Orthomyxoviridae* viruses cause the common influenza and influenza-like infections in humans and other mammals. These viruses contain negative single-stranded RNA as the genetic material and usually in eight segments. Included are influenza types A, B, and C as well as avian flu virus (H5N1).

The influenza virus infects the respiratory tracts of millions of people every year and is the cause of about 20,000 deaths annually in the U.S. The remarkable success of the influenza virus is due to genus *Orthomyxoviridae*'s ability to undergo genetic reassortment to produce antigenic shift among its three types (species), A, B, and C, and within substrains. The genome of the *Orthomyxoviruses* is typified by eight segments of single-strand negative-sense RNA protected within a nucleocapsid structure. Each of the eight segments of the single-stranded negative-sense RNA codes for a particular viral protein: virion surface glycoproteins, hemagglutinin and neuraminidase for attachment process to the host cell surface receptor; matrix 1 and matrix 2 proteins for ion channel; PA, PB1, and PB2 for transcriptase and replicase enzymes for transcription and replication of viral genome; nucleocapsid, NP protein, for protection of all the viral genome segments from degradation by host RNase (FIG. 1). This nucleocapsid gene has a highly conserved region, and therefore, holds promise as a target against which an effective antiviral strategy can be developed.

RNA interference (RNAi) is a recently discovered and developed antiviral strategy in which gene silencing is effected by homologous short (21–23 bp) dsRNA fragments known as short interfering or siRNA. When a long dsRNA is introduced into a cell line, the cellular enzyme called Dicer will cleave it into short interfering RNA (siRNA) molecules. This short interfering RNA molecule is now called the guided RNA. The guided RNA will guide the RNA-lnduced-Silencing-Complex (RISC) to the homologous target mRNA. Once it forms a hybrid structure to the homologous mRNA, the RISC will cleave the mRNA. As a result, protein that is encoded by the mRNA will no longer be produced and this will cause the silencing of the gene.

A recently published patent application, U.S. Patent Application Publication No. US 2004/0242518 A1 to Chen et al., published Dec. 2, 2004, discloses a siRNA (FIG. 21A, NP 1496) which partially overlaps the siRNA of this invention and cleaves at a different target nucleotide.

SUMMARY OF INVENTION

Briefly, this invention comprises a siRNA sequence against the constant region of the influenza virus nucleoprotein gene comprising:

```
Sense strand:      5' UGAAGGAUCUUAUUUCUUCdTdT 3'
Anti sense strand: 3' dTdTACUUCCUAGAAUAAAGAAG 5'
``` said sequence being inhibitory against influenza virus in animals including humans.

The two longer siRNA sequences, while useful, were found to have somewhat lesser efficacies were:

```
Sense strand:
5' UGAAGGAUCUUAUUUCUUCGGdTdT 3'     (SEQ ID NO: 3)

Anti sense strand:
3' dTdTACUUCCUAGAAUAAAGAAGCC 5'     (SEQ ID NO: 4)
``` and

```
Sense strand:
5' GGAUCUUAUUUCUUCGGAGACdTdT 3'     (SEQ ID NO: 5)

Anti sense strand:
3' dTdTCCUAGAAUAAAGAAGCCUCUG 5'     (SEQ ID NO: 6)
```

Both these siRNA preparations were 23 bp in length.

The invention further includes one or more of said siRNA sequences in the form of an aqueous suspension suitable for nasal inhalation.

Still further, the invention includes one or more of said siRNA sequences in the form of a plasmid expressing intracellularly in animals including humans.

In another aspect, the invention includes one or more of said siRNA sequences in the form of an AAV vector adapted to express intercellularly and establish a permanent inhibitory effect against influenza virus by integrating to the cellular chromosome of animals including humans.

In yet another aspect, the invention also includes the administration to an animal including humans, in a therapeutically effective amount, at least one of said siRNA sequences.

The objective of this study is to develop an antiviral therapeutic utilizing siRNA technology to target the constant region of the influenza virus nucleocapsid gene. Since influenza virus is a negative ss RNA virus, our specifically designed siRNA against NP gene would have dual inhibitory effect. The sense strand of the siRNA would directly cleave the viral genome and the anti-sense strand would target and cleave the homologous mRNA causing post transcriptional gene silencing.

Strategy to Design and Develop the siRNA against Influenza Virus NP Gene

Influenza is an enveloped virus with segmented single stranded negative RNA as the genetic material. The influenza virus contains eight segments or seven segments of (−) single stranded RNA genomes depending on two genera: influenza A and B viruses, and influenza C virus. Influenza A and B contain eight segments (−) of single stranded RNA genomes whereas the influenza C virus contains only seven (−) single strands of RNA as genome. The major distinction between influenza A, influenza B, and influenza C are the antigenic differences between their nucleoproteins (NP) and matrix proteins (M). The NP is the major structural protein that interacts with all the viral RNA segments, forming the viral ribonucleoprotein (RNP) complex.

The virology community tends to focus almost exclusively on two targets in the viral genome, the neuraminidase and hemoglobinase genes. It has been observed that an alternative gene coding for the NP protein possesses characteristics that suggest a greater suitability as a drug target. Neuraminidase and hemagglutinin, for instance, are known to be variable across different strains of flu. Therapeutics designed to target one form of neuraminidase gene or its protein product, therefore, might not be effective against a flu strain with a different form of the gene. Certain NP gene sequences, however, appear to be more highly conserved across different strains of flu, thereby permitting for the possibility of therapeutics targeting the gene or its protein to be effective against a broad spectrum of strains. In addition, the NP gene plays an extremely important role in the survival of the influenza virus by protecting all of its segments of the viral genome. A therapeutic substance diminishing or eliminating the NP gene or its protein product's ability to protect the viral genome should therefore leave the virus more susceptible to attack by the host's defenses.

Both the viral (−) strand RNA and the template (+) strand RNA are closely associated with the nucleocapsid; however, the mRNA (+) strands are not encapsidated. This close association of the NP to the viral RNA is to encapsidate the viral genome and perhaps protect it from the host RNase. Furthermore, it appears that NP is one of the most important proteins in the influenza virus structure since the virus must form ribonucleoprotein (RNP) complexes with all the genomic RNA segments. Therefore, it is likely that the best antiviral strategy is to target the NP gene of the influenza virus. Since influenza virus genomes undergo considerable changes, the siRNA of this invention was designed encompassing the conserved region of NP gene of influenza virus.

THE DRAWINGS

An enlarged drawing of influenza virus is shown in FIG. 1. This drawing is generic to influenza types A, B and C.

An enlarged view of influenza virus RNP is shown in FIG. 2.

DESCRIPTION OF PREFERRED EMBODIMENTS

Figure 1:
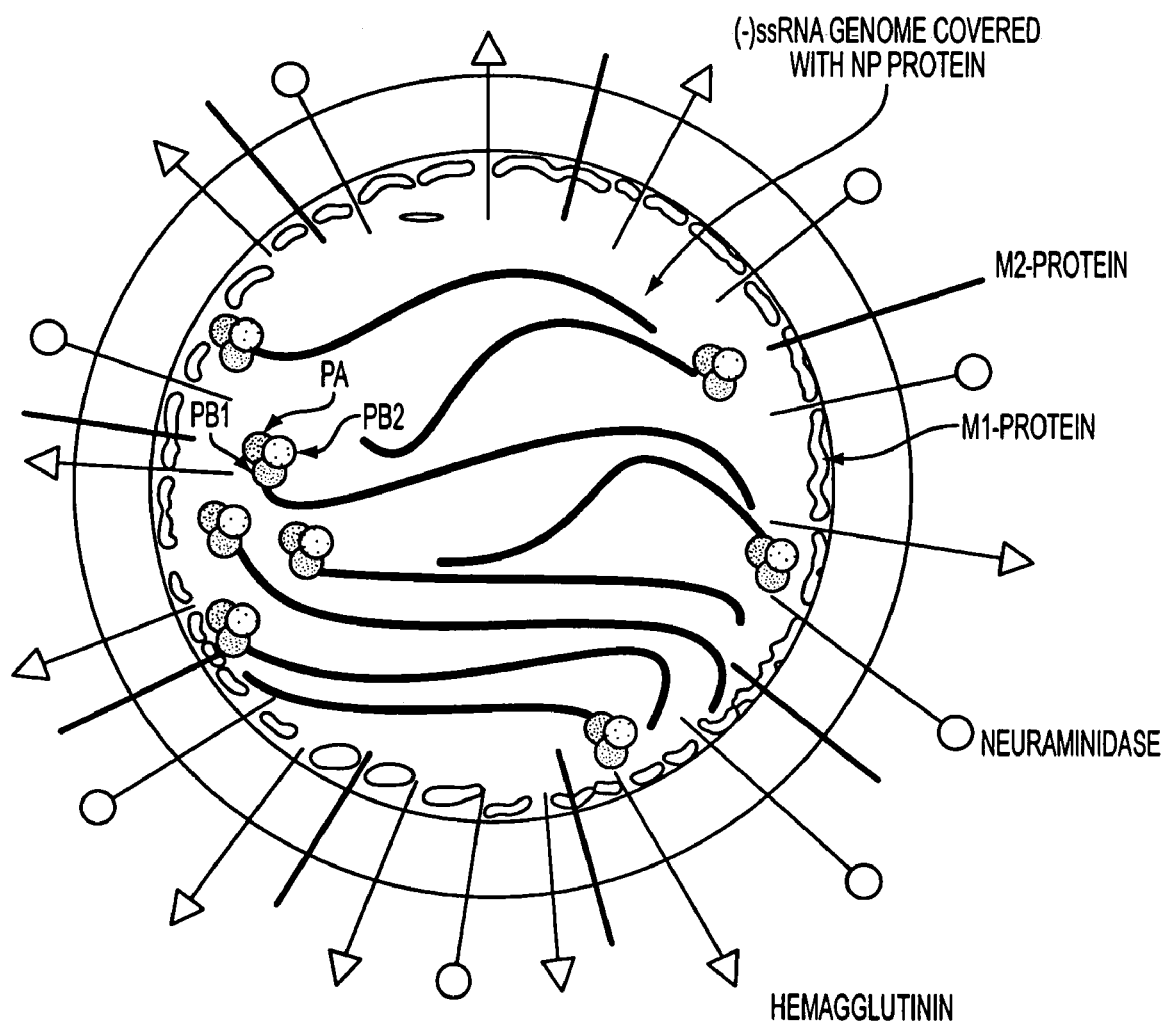
Figure 2:
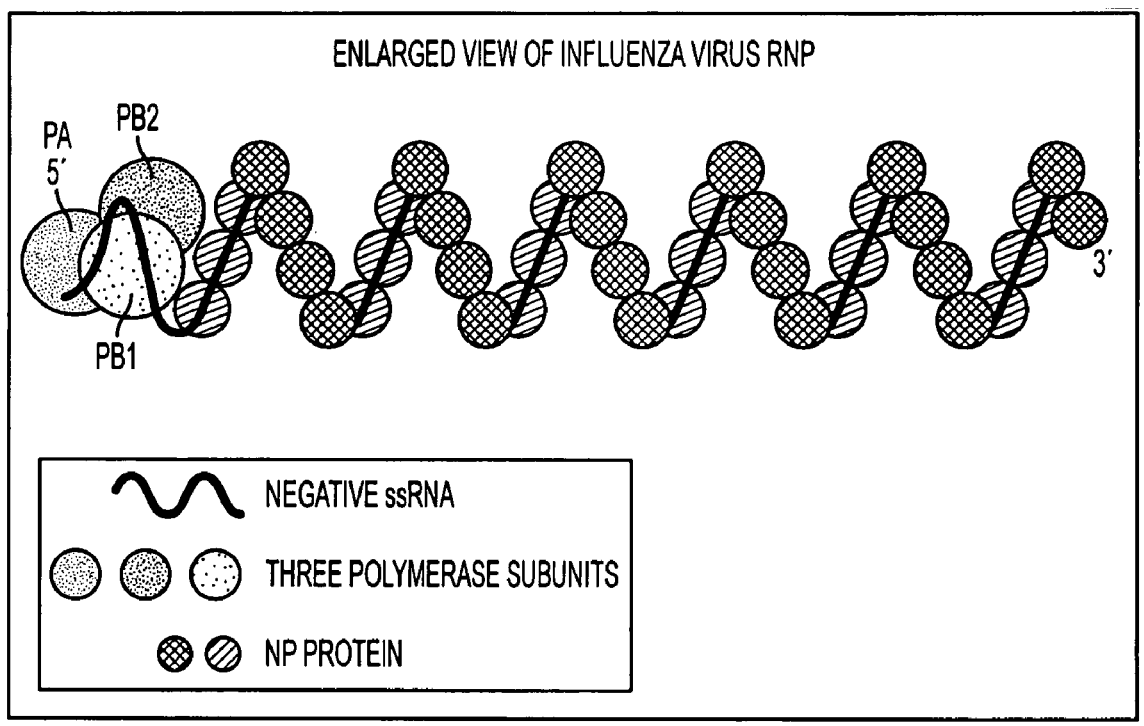
Figure 3:
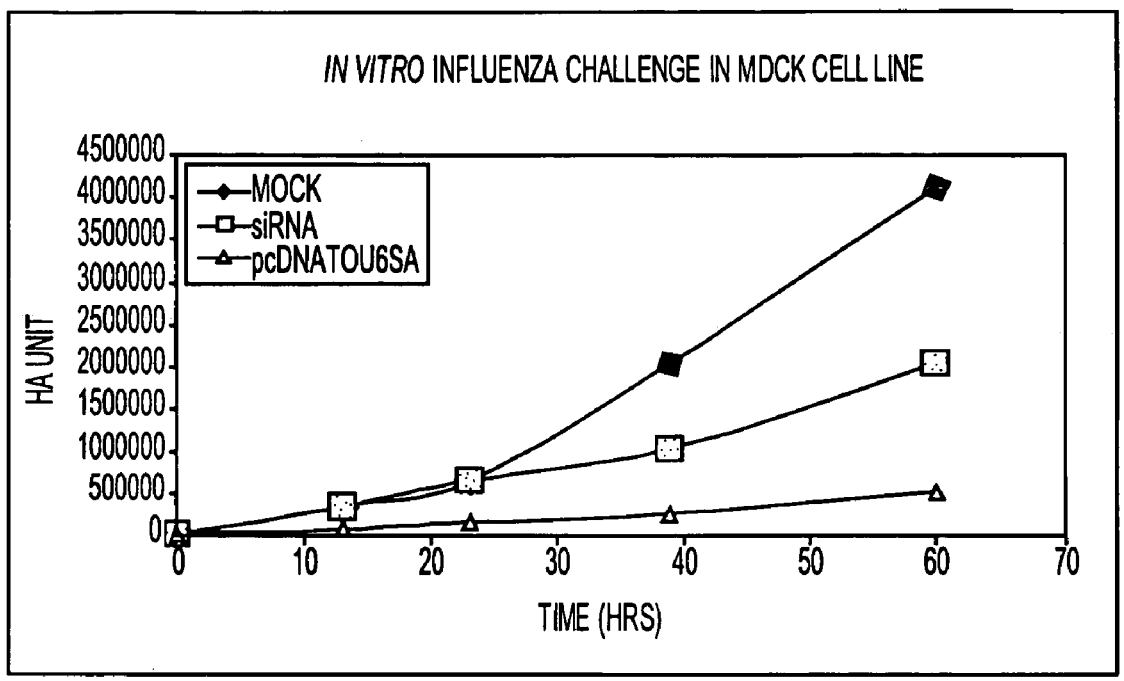
FIG. 3 is a bar graph further explained in Example 1.
Figure 4:
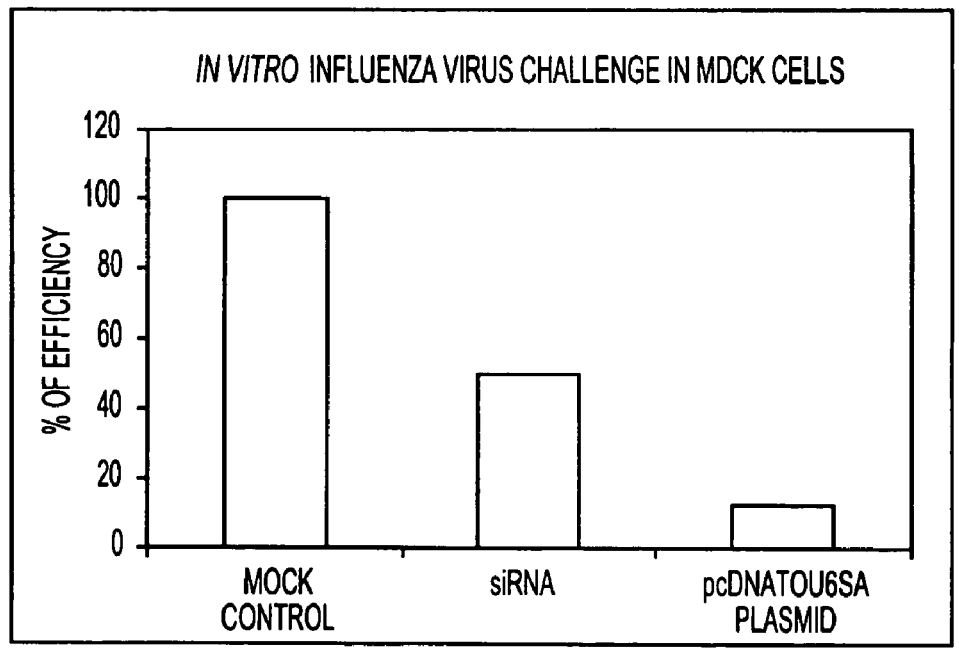
FIG. 4 is a bar graph also explained in Example 1.
Figure 5:
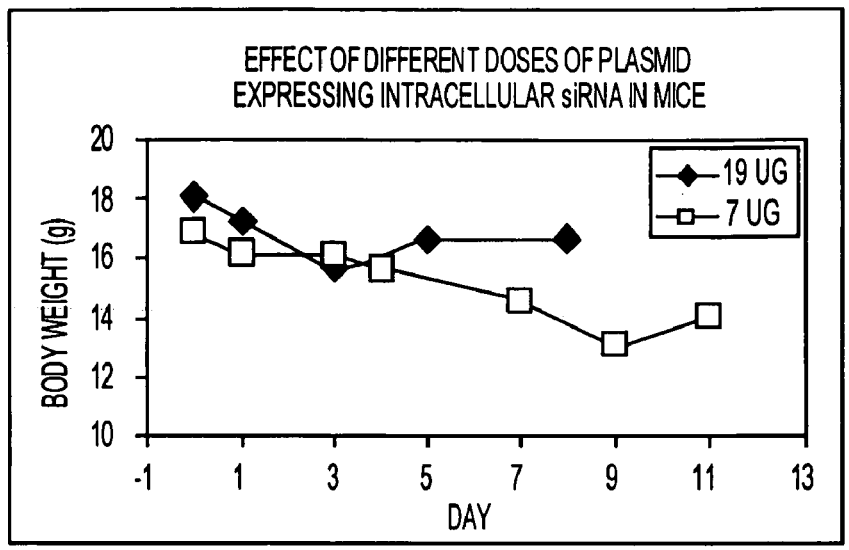
FIG. 5 is a bar graph further explained in Example 2.
Figure 6:
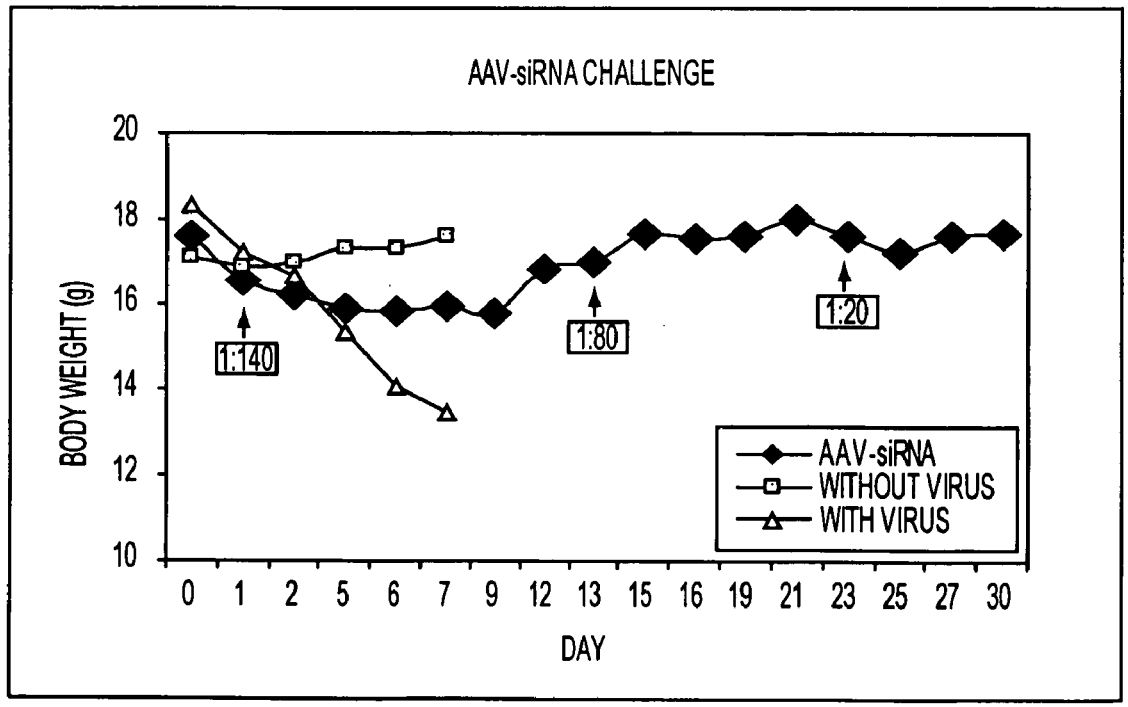
FIG. 6 is a bar graph explained in Example 3.

From the GeneBank database, the NP gene sequence of more than 20 different influenza virus isolates was aligned and the non-variable region of these sequences (nucleotides 1491–1538) identified. From the secondary structural analyses of this region of the viral genome, the sequence of the siRNA which has been found to be inhibitory of the influenza virus in animals including humans was identified.

The siRNA sequences of this invention, 19 to 23 nucleotides long, are based on the NP gene. The first in vivo experiment entailed dosing healthy mice (Balb/c) with plasmids or siRNA vectors containing the lead siRNA therapeutic (19 nucleotides long). After 24 hours, the mice were challenged with strains of murine flu virus (X88 and PR8) normally considered to be less pathogenic, but in this case, engineered to exhibit a high degree of virulence. The exposed mice were weighed to determine any loss of body mass, an endpoint used in place of lethality. It was found that even small doses prevented signs of infection throughout the two to three weeks of the study.

In a separate experiment healthy mice were infected with lethal doses of influenza virus and after 24 hours they were treated with plasmid expressing siRNA. It was found that this therapeutic approach also protected all the experimental mice.

The NP gene regions of avian flu were also compared with the siRNA sequences of this invention. Among the 50 isolates of H5N1 studied, all 50 showed 100% homology with the NP regions corresponding to the siRNA of this invention, suggesting they would be effective against avian flu.

Development of Different Forms of siRNA

The preferred siRNA of this invention was developed in three forms:

(1) Twenty one nucleotide sense and antisense RNA in duplex form having the sequence first identified above. This siRNA was synthetically made. The siRNA can be administered readily internasally in the form of a mist by inhalation. This results is an effective but relatively short useful life in the order of days. The mist is made up of the siRNA in the form of a cationic polymer (polyelhylenimine) medium to provide a suspension.

(2) Plasmid expressing sense and anti-sense strands of the same siRNA under the influence of pol III promoter, U6+1. The promoter and the sequence encoding the sense strand followed by a TTTTT terminator, and the promoter, the sequence encoding the anti-sense strand of siRNA followed by TTTTT terminator was cloned into plasmid pcDNA4/TO. The plasmid expressing siRNA can also be administered intranasally in the form of a cationic polymer emulsion. The inhibitory effect produced by the plasmid has a longer life than the synthetic siRNA described in (1).

(3) AAV vector expressing sense and anti-sense strands of the same siRNA under the influence of pol III promoter, U6+1. The AAV vector is a benign virus vector which enters the cell of the host and integrates into the cellular chromosome, and expresses siRNA constitutively to yield a permanent inhibitory effect against influenza virus in the host.

This invention provides novel short-interfering RNA (siRNA) sequences targeting a highly conserved region of the influenza viral genome. The most effective siRNA target sequence was found to be within the nucleoprotein gene, one of the eight genes comprising the influenza genome. The preferred siRNA, 19 base-pairs long, was evaluated by introducing it into mice later infected with a murine flu virus. Weight loss, was used as the primary endpoint of the studies. Weight loss was not observed in the experimental infected mice.

The following Examples are illustrative:

EXAMPLE 1

Graphs 3 and 4 demonstrate the efficacy of siRNA in commercially available MDCK cell cultures. The vertical axis indicates the level of influenza virus. The horizontal axis indicates time (hours). The line indicated as blue shows the results over time for a control in which no siRNA is added to the cell culture. The line indicated in red shows the results over time when the synthetic si RNA in aqueous suspension was transfected to the cell culture. The line indicated in green shows the results over time when siRNA in plasmid form was transfected to the cell culture. Twenty four hours after transfection cells were infected with influenza virus.

Graph 4 presents the results shown in Graph 3 in bar form and shows the inhibitory effect of siRNA in synthetic and plasmid form when compared to the control.

EXAMPLE 2

Graph 5 shows the results conducted in a standard laboratory mouse (Balb/c) model. The vertical axis expresses the average body weight in five (5) mice. The horizontal axis is time expressed in days. The line indicated in blue shows the effect on the average weight of five mice administered internasally with the cationic lipid emulsion of the siRNA plasmid in a 19 µg/mouse dosage. The red line shows the results when the same emulsion was identically administered to five mice in a 7 µg dosage. In both cases, the dosage was administered at day "0". Thereafter, no further siRNA plasmid was given. At day "1", a lethal dose of influenza virus was given to both groups of mice. The effect on body weight was taken as a measure of efficacy. It is significant that at the higher dosage (blue line), the siRNA plasmid was almost completely effective in preventing loss of body weight, indicating that the siRNA plasmid is silencing the influenza virus nucleocapsid gene.

EXAMPLE 3

In Graph 6, the same mouse model was used. The brown line was a control group of five mice which received neither siRNA in any form nor was this group exposed to influenza virus. The line indicated as green shows the result with five mice who intranasally received siRNA in the AAV-siRNA form on day "0" and a lethal dose of the influenza virus at day "1". The line indicated as blue represents the results in five mice which received no siRNA in any form but did receive the influenza virus on day "1". As can be seen, the control (brown line) group continued to thrive and in fact continue to survive long past the end of the brown line, as was to be expected. The interesting results are seen when comparing the green and blue indicated lines. The influenza virus quickly killed all of the mice which had not received the siRNA in any form (blue indicated line). However, the mouse group receiving the AAV-siRNA followed by a lethal dose of influenza virus 24 hours later (green line) continued to thrive. Further, in Graph 4, the mouse group indicated by the green line was subsequently exposed to a doubled dosage of influenza virus on day 13 continued to thrive. Subsequently, the influenza virus dosage was doubled again on day 23 and the same five mice continued to thrive, thus indicating that the AAV-siRNA had established a permanent inhibitory effect against the influenza virus in these mice.

The invention consists of, consists essentially of, and comprises the above nucleotide sequences in all forms in which said sequences are the therapeutically active agent. Normally, the sequences are isolated and purified and used in pharmaceutical carriers, or incorporated into plasmids or vectors. The techniques for the preparation of such pharmaceutical compositions, the incorporation of the nucleotide sequences into plasmids and vectors can be carried out by those of ordinary skill in this art.

In regard to the effective therapeutic dose, it is somewhat difficult to ascertain at this time. However, from the mouse experiment with plasmid form of siRNA and challenge with a lethal dose of influenza virus, we estimate about 2–3 μg/kg body weight may be the effective therapeutic dose against the influenza virus infection in animals including humans. The same dosages are deemed effective for the vector form. The siRNA suspension is also useful around this dosage range.

The invention claimed is:

1. A siRNA sequence against the constant region of the influenza virus nucleoprotein gene comprising:

```
Sense strand:
5' UGAAGGAUCUUAUUUCUUCdTdT 3'    (SEQ ID NO: 1)

Anti sense strand:
3' dTdTACUUCCUAGAAUAAAGAAG 5'    (SEQ ID NO: 2)
``` said sequence being inhibitory against influenza virus in animals including humans.

2. The siRNA sequence of claim 1 in the form of an aqueous suspension suitable for nasal inhalation.

3. The siRNA sequence of claim 1 in the form of a plasmid expressing intracellularly in animals including humans.

4. The siRNA sequence of claim 1 in the form of an AAV vector adapted to express intercellularly and establish a permanent inhibitory effect against influenza virus by integrating to the cellular chromosome of animals including humans.

5. A method comprising the administration to an animal including humans of a therapeutically effective amount of the siRNA sequence of claim 1.

6. The method of claim 5 wherein the administration is by nasal inhalation in the form of an aqueous mist.

7. The method of claim 5 wherein the administration is in the form of a plasmid.

8. The method of claim 5 wherein the administration is in the form of a AAV vector.

9. The method of claim 5 wherein the administration is in the form using plasmid pcDNA4/TO.

10. The method of claim 5 wherein the administration is effective against influenza virus A, B or C.

11. The method of claim 5 wherein the administration is effective against avian influenza (H5N1).

* * * * *

UNITED STATES PATENT AND TRADEMARK OFFICE
CERTIFICATE OF CORRECTION

PATENT NO. : 7,199,109 B2
APPLICATION NO. : 11/445573
DATED : April 3, 2007
INVENTOR(S) : Bijay K. Pal and Lynn M. Tran It is certified that error appears in the above-identified patent and that said Letters Patent is hereby corrected as shown below:

Column 2, line 16: should read; <u>a)</u> Sense strand:
Column 2, line 23: should read; <u>b)</u> Sense strand:
Column 3, line 3: should read; and hemoglobinase <u>hemagglutinin</u>

Signed and Sealed this

Seventh Day of August, 2007

JON W. DUDAS
*Director of the United States Patent and Trademark Office*

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial
<220> FEATURE:
<223> OTHER INFORMATION: Sense strand of a short interfering dsRNA
      molecule targeting the constant region of the influenza virus
      nucleoprotein gene

<400> SEQUENCE: 1
ugaaggaucu uauuucuuct t                                              21

<210> SEQ ID NO 2
<211> LENGTH: 21
<212> TYPE: DNA
<213> ORGANISM: Artificial
<220> FEATURE:
<223> OTHER INFORMATION: Antisense strand of the short interfering dsRNA
      molecule targeting the constant region of the influenza virus
      nucleoprotein gene of SEQ ID NO:1

<400> SEQUENCE: 2
gaagaaauaa gauccuucat t                                              21

<210> SEQ ID NO 3
```

-continued

```
<211> LENGTH: 23
<212> TYPE: DNA
<213> ORGANISM: Artificial
<220> FEATURE:
<223> OTHER INFORMATION: Sense strand of a short interfering dsRNA
      molecule targeting the constant region of the influenza virus
      nucleoprotein gene

<400> SEQUENCE: 3
ugaaggaucu uauuucuucg gtt                                             23

<210> SEQ ID NO 4
<211> LENGTH: 23
<212> TYPE: DNA
<213> ORGANISM: Artificial
<220> FEATURE:
<223> OTHER INFORMATION: Antisense strand of the short interfering dsRNA
      molecule targeting the constant region of the influenza virus
      nucleoprotein gene of SEQ ID NO:3

<400> SEQUENCE: 4
ccgaagaaau aagauccuuc att                                             23

<210> SEQ ID NO 5
<211> LENGTH: 23
<212> TYPE: DNA
<213> ORGANISM: Artificial
<220> FEATURE:
<223> OTHER INFORMATION: Sense strand of a short interfering dsRNA
      molecule targeting the constant region of the influenza virus
      nucleoprotein gene

<400> SEQUENCE: 5
ggaucuuauu ucuucggaga ctt                                             23

<210> SEQ ID NO 6
<211> LENGTH: 23
<212> TYPE: DNA
<213> ORGANISM: Artificial
<220> FEATURE:
<223> OTHER INFORMATION: Antisense strand of the short interfering dsRNA
      molecule targeting the constant region of the influenza virus
      nucleoprotein gene of SEQ ID NO:5

<400> SEQUENCE: 6
gucuccgaag aaauaagauc ctt                                             23
```